United States Patent [19]

Gaafar et al.

[11] Patent Number: 4,564,592
[45] Date of Patent: Jan. 14, 1986

[54] TOXOPLASMOSIS FACTOR AND PRODUCTION OF SAME

[75] Inventors: Hassan A. Gaafar, Voorheesville; Brian G. Grimwood, Delmar, both of N.Y.

[73] Assignee: Research Corporation, New York, N.Y.

[21] Appl. No.: 460,057

[22] Filed: Jan. 21, 1983

[51] Int. Cl.⁴ .................... C12P 21/00; A61K 39/002
[52] U.S. Cl. ........................................ 435/68; 424/88
[58] Field of Search .................. 424/88, 92, 93, 89; 435/68; 260/112 R

[56] References Cited

PUBLICATIONS

Chemical Abstracts, vol. 98, Abst. No. 3350y, 1983.
Chemical Abstracts, vol. 95, Abst. No. 130760v, 1981.
Weinman et al., Yale J. Biol, Med., vol. 22, pp. 323–326, 1950.
Woodworth et al., J. Inj. Diseases, vol. 107, pp. 318–324, 1960.
Lurde et al., J. Parasitol, vol. 50, pp. 49–51, 1964.
Arayo, F. et al., Immunology, vol. 27, pp. 711–720, 1974.
Krahenhuhl, J. et al., J. Immunology, pp. 425–431, 1972.
Remington, J. et al., Immunology of Parasitic Infections, pp. 259–263, ed. Cohen and Saden, Blackwell Scientific Publication, London.

Primary Examiner—Blondel Hazel
Attorney, Agent, or Firm—Scully, Scott, Murphy & Presser

[57] ABSTRACT

A vaccine for the prevention of congenital Toxoplasmosis and methods for its production.

3 Claims, 2 Drawing Figures

TOXOPLASMOSIS FACTOR AND PRODUCTION OF SAME

BACKGROUND OF THE INVENTION

Toxoplasmosis is a ubiquitous infection in nature. It is characterized as a severe generalized or CNS granulomatous disease caused by *Toxoplasma gondii*. Asymptomatic infections are common; serologic surveys show that worldwide 25–50% of adult populations are infected and have detectable antibodies to the etiologic agent.

When the disease is acquired after birth, it may be associated with mild, nonspecific signs and symptoms, or it may be completely asymptomatic, with antibodies in patient's sera as the only indication of exposure. A more acute and sometimes fatal infection occurs in immunologically compromised patients.

Congenital infection, on the other hand, can be devastating. In animals, primary infection during pregnancy results in abortion or low fertility. In humans the clinical manifestations of congenital toxoplasmosis appear to be related to the trimester of pregnancy during which the mother acquired the infection. Infection during the first trimester is commonly associated with stillbirth, perinatal death, or the more severe forms of congenital toxoplasmosis. Infection during the third trimester usually results in mild or subclinical infection.

This clinical picture, together with the observation that *Toxoplasma gondii* trophozoites are rarely isolated from aborted fetuses, suggests that congenital toxoplasmosis syndromes may occur when the fetus is exposed either to the trophozoites and/or to a toxic substance produced by the infection.

The description of a toxic substance formed in vivo in mice infected with *Toxoplasma gondii* was first reported by Weinman and Klatchko, "Description of toxin in toxoplasmosis", *Yale J. Biol. Med.* 22: 323 (1950). This toxin, termed toxotoxin, was found in the peritoneal exudate and was demonstrated by intravenous inoculation into normal mice. When sufficient centrifuged supernatant of the exudate was injected, usually 0.1 to 0.5 ml, convulsions and immediate death resulted. These authors reported that toxotoxin was destroyed by trypsin and was nondialyzable. It was found to be stable at room and refrigerator temperatures and was not altered by lyophilization procedures. Activity was not reduced by heating to 56° C. for 30 minutes, or to 100° C., although autoclaving temperatures diminished potency.

Lunde and Jacobs in *The Journal of Parasitology*, Vol. 50, No. 1, February 1964, p.49–51 describe the preparation of a crude toxoplasma lysate obtained by lysing washed, filtered parasites in sterile distilled water. The toxic activity is destroyed by trypsin. The toxic material can be salted out with 30% saturated $(NH_4)_2SO_4$ in the cold and has a high absorption peak at 260 M$\mu$. Heating the lysate at 56° C. for 15 minutes completely destroys its lethal effect. The lethal effect is noted only when the lysate is administered intraveneously to rabbits. Intraperitoneal inoculation in mice produced no effect.

BRIEF SUMMARY OF THE INVENTION

The present invention is based upon the discovery of a novel, hithero unreported, temperature sensitive, non-dialysable product termed Toxoplasma Factor (TF). The product, TF is believed to be a glycoprotein whose activity is sensitive to trypsin and pH extremes.

It is a reasonable assumption that TF occurs as part of the natural toxoplasma infection and is responsible for pathologic conditions.

In experimental animals, the following effects have been observed with this novel material:

(a) TF simulated the clinical picture of chronic *Toxoplasma gondii* infection, with loss of weight, ruffled fur and lethargy.

(b) The cell-free factor, like the intact organism, produced splenomegaly and involution of the thymus.

(c) When TF was intraperitoneally injected in fertile mice, experimental females failed to produce litters in the first two ovulation cycles. If pregnancy occurred and continued to term, the number of animals in each litter and/or the number reared to maturity was reduced.

The above observations were transient, however, as treated females could not be differentiated from controls 5–6 weeks later.

(d) Animals injected with the crude preparation, while experiencing the transient signs of acute infection, developed an apparent immunity to challenge with TF which lasted for at least 242 days.

(e) Injection of diluted (1:1000) TF intraperitoneally on the 7th or 8th day of pregnancy resulted in congenital deformities and low birth weight in 90–100% of fetuses.

(f) These congenital deformities were prevented by active immunization of females 4–6 weeks earlier with the crude preparation or passively by inoculation with rabbit antisera to TF.

As discussed more in detail hereinafter, it is also within the scope of the present invention to prepare a vaccine from this novel material and/or to prepare a toxoid which may be used to immunize humans and domestic animals to help control congenital toxoplasmosis.

DETAILED DESCRIPTION OF THE INVENTIION

Figure 1:
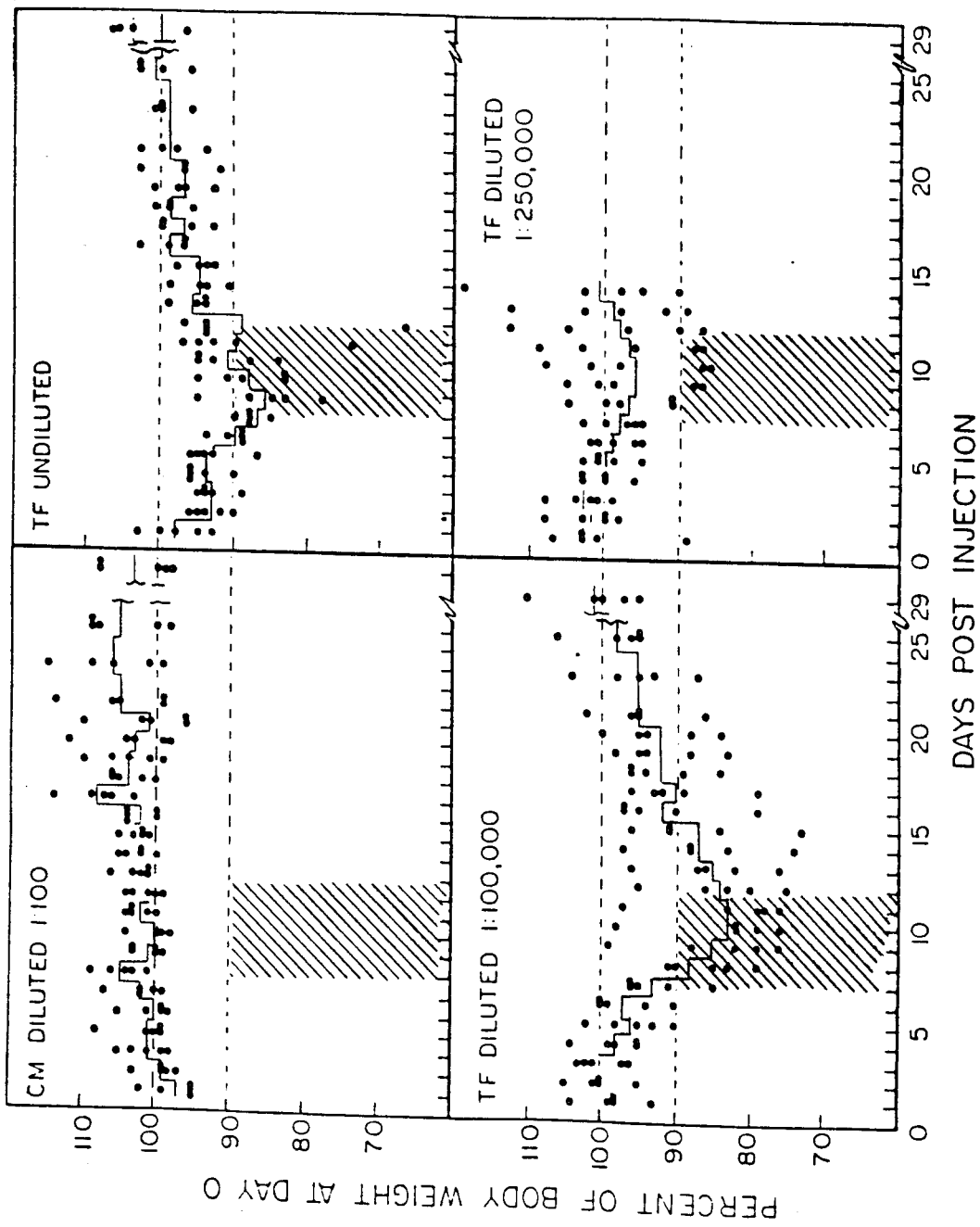

In carrying out the present invention, *Toxoplasma gondii* trophozoites were maintained by passing twice weekly in mice. Phosphate buffered saline (PBS) (pH 7.2) was used to suspend the trophozoites in the peritoneal cavity of the mice. The serial passage is from infected to non-infected mice.

TF Production

Cell cultured trophozoites were propagated in vitro in Baby Hamster Kidney (BHK-21) cells, grown in suitable culture flasks with Modified Essential Medium and Earle's salts and 5% fetal bovine serum, from aseptic isolations of mouse peritoneal fluid. The cultures were incubated at 37° C. for 3–4 days before inoculation. After incubation, the primary trophozoite culture was used to inoculate freshly confluent monolayer cell cultures from which TF was obtained. Because of the ubiquitous nature of the parasite, TF could be obtained from a variety of cell cultures, media and containers. It has been produced from human embryonic lung cultures infected with toxoplasma. It is assumed that TF could also be obtained from infected animals. Obviously, there may be one or more serial passages of the organism in cell cultures.

TF Harvest

The monolayers were destroyed in 3–4 days, at which time the used culture medium containing host cellular debris and trophozoites was centriguged at 5,000×g for 10 minutes, 4° C. to pellet the particulate matter. The supernatant was filtration sterilized by passing through 0.22μ pore diameter Sterivex-GS filter units. The sterile medium containing TF was then stored by refrigeration or freezing in liquid nitrogen.

Sterility Testing

Each lot of TF containing medium was routinely tested for bacterial contamination by plating on bacterial culture medium. The used medium was also examined for mycoplasma using DNA fluorochrome staining and for viruses on negatively stained grids and examination by electron microscopy.

Control Medium (CM)

The medium used to inject control groups of mice was prepared by using the medium and typed cells from uninfected BHK-21 cultures. Eight to 10 day old cultures were used for this material. The used medium was poured from the flasks, the flasks were rinsed with 10 ml of sterile water and the rinse was combined with the used medium. Ten more ml of $H_2O$ were added to each flask which were then capped and incubated overnight at 37° C. This lysate material was added to the used medium container then handled exactly as the TF containing medium.

Assay for TF Activity

An in vivo assay (Weight Loss Assay, WLA) using mice was developed to test for the weight loss effect of TF containing material, One biological unit is defined as that amount of TF present in 0.5 ml which when injected intraperitoneally into non-immune mice (NYA:-Nylar strain, females weighing between 22–28 g) will elicit at least a 10% body weight loss in 80% of the mice for 2 consecutive days between days 7 and 12 post injection (day of injection, day 0).

The amount of TF activity in any given production lot or function is determined by endpoint titrations.

Dilutions of materials were made by placing aliquots into 100 ml volumetric flasks and adding saline, pH 7.2 PBS. Drummond Dialamatic Microdispensers were used to dispense the aliquots.

The test materials were held on ice until injected into mice, the same day the diluations were made. The mice were weighed on an electronic top loading balance just prior to intraperitoneal injection using sterile 1 cc tuberculin syringes and 26 ga. ⅜ inch needles. In most instances weights were determined only on the day of injection (day 0) and days 7 through 12 post injection.

Chemical and Physical Properties of TF

Partial Purification of TF by Lectin Affinity Chromatography (ConATF)

Medium containing TF was placed directly onto ConA-Sepharose 4B columns previously equilibrated with PBS. The used medium containing TF or the CM was passed through the void column and the flow was stopped for 1 hour at room temperature. PBS was added and the first 10 ml fraction was collected as was a fraction after 5–10 ml void columns had passed through the column. The flow rate was adjusted to about one half ml per minute. α-methyl-D-mannoside (0.5M) in PBS was added and allowed to pass through the void column. The flow was stopped for 2 hours after which the elution fractions were collected. Elution fractions of ConATF and ConACM were sterilized using Millex-GV filter units and aliquots were taken for WLA with the remainder stored frozen until needed.

The results of Concanavalin A-Sepharose 4B affinity chromatagraphy indicate TF is retained and eluted with α-methyl-D-mannoside. When sufficient volumes of used medium containing TF were added to the columns, a small amount of TF could be found in the first void column. Subsequent fractions from washing the columns with PBS contained no TF activity. When α-methyl-D-mannoside was passed throught the column, TF was recovered in the elution fractions. As little as 0.04M and as high as used, (0.5M) α-methyl-D-mannoside eulted TF as determined by WLA. Approximately a 10-fold increase in purity based upon the units of activity by WLA per mg protein recovered in 10 ml 0.5M mannoside elution fraction. The symptoms produced by the mannoside elution fractions (ConATF) were identical to that of the crude TF in the used culture medium. The results are shown in Table 1 below.

TABLE 1

ToxoFactor activity as determined by Weight Loss Assay in α-methyl-D-mannoside elution fraction from Concanavalin A-Sepharose 4B affinity columns

| Fraction | Units of activity/ml | Units of activity/mg protein* |
|---|---|---|
| Pre-column (10 ml) | $2 \times 10^6$ | $8 \times 10^4$ |
| 1st void column (10 ml) | 0 | — |
| 1st PBS wash (10 ml) | 0 | — |
| 10th PBS wash (10 ml) | 0 | — |
| 1st elution (10 ml) with 0.5 M mannoside | $2 \times 10^4$ | $5 \times 10^5$ |

*Protein was quantitated by the Bio-Rad Protein Assay System using bovine serum albumin as the standard.

Heat lability of TF and ConATF

Medium containing TF was placed for up to 1 hour in a 56° C. or 37° C. water bath. Aliquots were removed at different times for the WLA. A volume of TF was held at 4° C. as the test control.

Lability of TF and ConATF at pH 2, 5, 7, 9 and 12

The pH of used medium containing TF activity was adjusted to pH 2 or pH 5 using 1M HCl and pH 9 or pH 12 with 1M NaOH. After storing refrigerated overnight the material was neutralized with 1M NaOH or 1M HCl. CM and ConACM was treated similarly. Fractions were held at 4° C. (pH 7.0) was used to determine TF activity as 100%.

Centrifugation of TF and ConATF

Used medium containing TF and ConATF were centrifuged at 100,000×g for 1 hour in an L5-65B ultracentrifuge with an SW 50.1 rotor using cellulose nitrate tubes. As a control, tubes with TF medium were held without centrifugation at 4° C. for the same period. The supernatant and fractions were removed and the tubes rinsed with 5 vols., PBS. Two ml PBS was added per tube and vortexed for several minutes. The supernatant and "pellet" fractions were then examined for TF activity by WLA.

Trypsinization of TF

The used medium containing TF activity was incubated with trypsin (bovine pancreas, type III) at a concentration of 0.3 mg per ml solution for 4 hours, 37° C. This material plus a similar control fraction except with no trypsin was injected into mice for WLA.

The results of the effect of the treatments upon TF are shown in Table 2.

TABLE 2

ToxoFactor activity as determined by Weight Loss Assay after various treatments

| Treatment | Percent of Original Activity[a] |
|---|---|
| None | 100 |
| 56° C. 15 minutes | 20 |

TABLE 2-continued ToxoFactor activity as determined by Weight Loss Assay after various treatments

| Treatment | Percent of Original Activity[a] |
|---|---|
| 56° C. 45 minutes | 0 |
| 37° C. 4 hours | 25 |
| Trypsin, 37° C. | 10 |
| pH 2, 8° C. 18 hours | 0 |
| pH 5, 8° C. 18 hours | <50 |
| pH 7, 8° C. 18 hours | 100 |
| pH 9, 8° C. 18 hours | 100 |
| pH 12, 8° C. 18 hours | 0 |
| Supernatant (100,000 × g, 1 hour 4° C.) | 50 |
| "Pellet" (100,000 × g, 1 hour 4° C.) | 50 |
| "Pellet" (1 × g, 1 hour 4° C.) | 50 |
| Filtrate (Diaflow, PM 10) | 0 |
| Filtrate (Diaflow, YM 30) | 0 |
| Filtrate (Diaflow, XM 50) | 50 |
| Filtrate (Diaflow XM 100A) | 50 |
| −196° C., 3 months | 100 |

[a]Both unfractionated TF (as in used medium) and ConATF tested. Trypsin and −196° C., TF only.

Biological Characterization of TF

In the production lot tested as shown in FIG. 1, the dilution of 1:100,000 of TF was the highest effective dilution, an endpoint being reached at 1:200,000. This undiluted material by definition contained $10^5$ units of TF per 0.5 ml dose. Typically, as in FIG. 1, higher doses of TF tend to produce a slightly faster response and recovery than the lower doses.

The accompanying FIG. 1 shows the body weight loss induced by TF. Adult NYA:Nylar female mice weighing between 22 and 28 grams were injected intraperitoneally with 0.5 ml of material. TF was used medium from Toxoplasma infected cell BHK-21 cultures and CM was used medium from uninfected water lysed BHK-21 cells. The mice were weighed on an electronic top-loading balance just prior to injection and on subsequent days as indicated by the symbol ●. The horizontal lines between ●'s indicate the means weights.

Mice administered TF intraperitoneally, intravenously or intragastrically all produced similar symptoms and weight loss.

Figure 2:
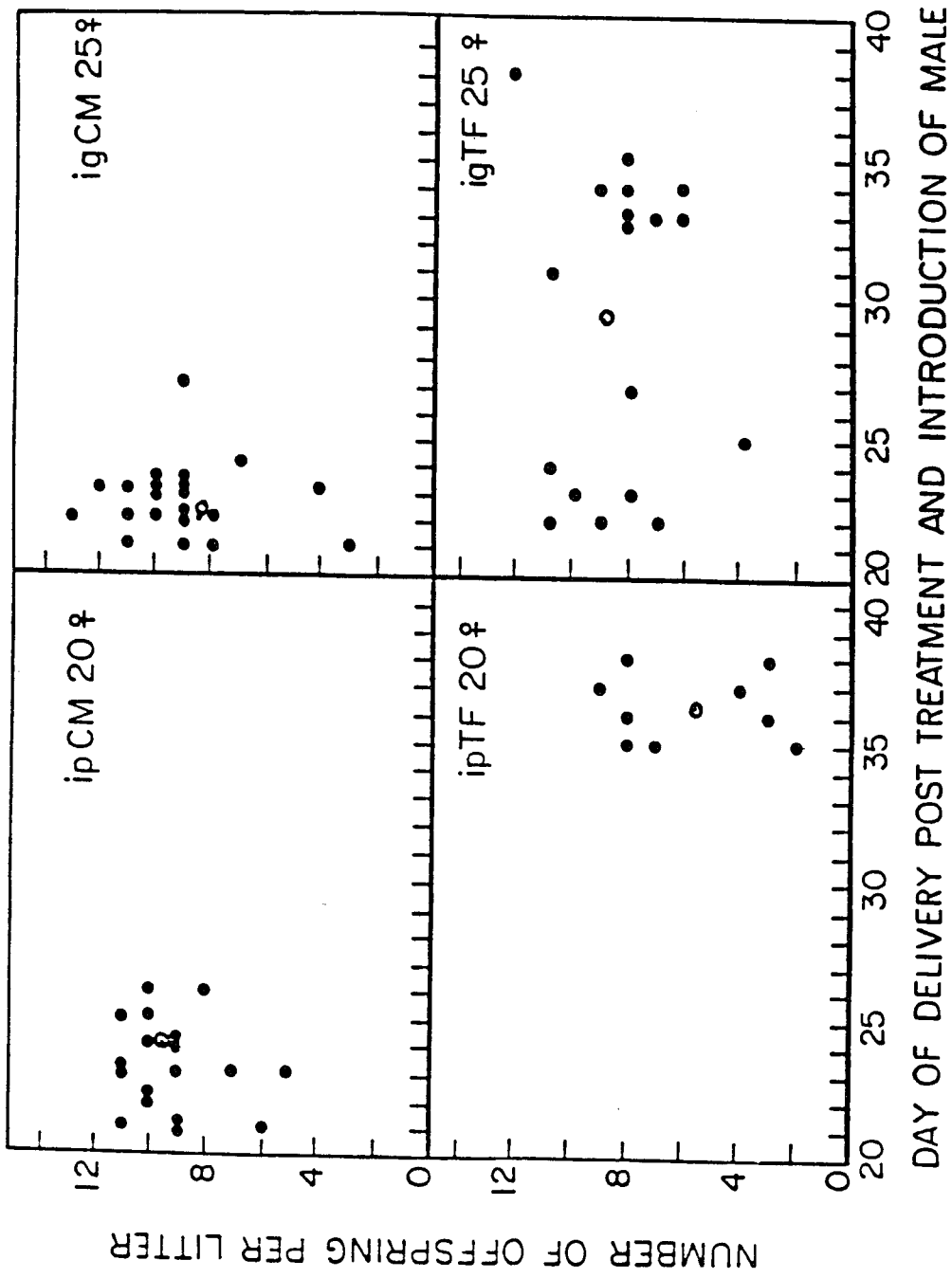

The accompanying FIG. 2 shows the reproductive losses in female mice treated with ToxoFactor the same day males were introduced. Each littter is represented by an individual point, ○ as the day of parturition and the number of live newborn (≦24 hours old). The symbol ⊙ indicates the mean litter age and day of delivery. Treatment of adult virgin females was by intraperitoneal injection of $10^4$ units (20 females) or by intragastric intubation of $10^5$ units (25 females) of ToxoFactor weight loss activity delivered in 0.5 ml. Pairing of females and males was for 18 days. Controls were similar mice given CM either intraperitoneally or intragastrically.

These data show that TF administered intraperitoneally prevented completely the delivery of litters from conception within the firt two weeks post injection/pairing. Those females which delivered liveborn (within 24 hours of delivery) as a result of conception in the third week post injection/pairing produced fewer per litter (5.8) than did the CM injected controls (9.2). When less than one TF WLA unit was injected into females on day zero of male:female pairing, reproduction losses were less severe than with higher doses as shown in Table 3.

TABLE 3

Reproduction losses in female mice exposed to ToxoFactor

| I.P. Injection of Females | Number of Female/male Pairs 18 Days | Number of Females Delivering Live Offspring | Mean Day of Delivery | Newborn <24 Hr Old Total Number | Newborn <24 Hr Old Mean Number per Litter | Surviving Offspring 3 Weeks Old Total | Surviving Offspring 3 Weeks Old Mean Number Per Litter | Mean Number Offspring Surviving to 3 Weeks Per Paired Female |
|---|---|---|---|---|---|---|---|---|
| Day 0 | | | | | | | | |
| 8 units TF | 9 | 6 | 36 | 37 | 6.2 | 33 | 5.5 | 3.7 |
| 1 unit TF | 8 | 6 | 30 | 37 | 6.2 | 26 | 4.3 | 3.3 |
| 0.4 unit TF | 10 | 7 | 23 | 62 | 8.9 | 45 | 6.4 | 4.5 |
| 0.2 unit TF | 10 | 10 | 31 | 91 | 9.1 | 85 | 8.5 | 8.5 |
| CM | 9 | 8 | 23 | 69 | 8.6 | 59 | 7.4 | 6.6 |
| None | 9 | 7 | 22 | 67 | 9.6 | 60 | 8.6 | 6.7 |
| Day 7 | | | | | | | | |
| 8 units TF | 20 | 1 | 24 | 8 | 8 | n.d. | n.d. | n.d. |
| 1 unit TF | 20 | 1 | 26 | 6 | 6 | n.d. | n.d. | n.d. |
| CM | 40 | 34 | 22 | 229 | 8.8 | n.d. | n.d. | n.d. |
| Day 0 | | | | | | | | |
| 10 units ConATF | 20 | 18 | 34 | n.d. | n.d. | 116 | 6.4 | 7.0 |
| ConACM | 20 | 19 | 29 | n.d. | n.d. | 139 | 7.3 | 5.8 |
| Day 7 | | | | | | | | |
| 10 units ConATF | 20 | 0 | 0 | n.d. | n.d. | 0 | 0 | 0 |
| ConACM | 20 | 17 | 23.4 | n.d. | n.d. | 130 | 7.6 | 6.8 |

Actively Acquired Protection Against TF Adult Symptons and Reproductive Failure

Mice which had been exposed to TF intraperitoneally were symptom-free after challenge with similar material as early as 21 days and as late as 242 days after the first exposure (Table 4). Mice which had experienced the initial symptoms with as little as 1 unit TF were protected against as much as $10^3$ units. No protection was found in mice originally exposed to CM in any form or to TF inactivated by heat or pH when the animals were challenged with active TF.

Reproductive losses in immunized females (intraperitoneal TF) were prevented when challenged with TF the same day male/female pairing (18 days) was begun.

Prior exposure of female mice to ConATF also was highly efficient in preventing the toxic symptoms in the adults and fetal damage when challenged with similar material.

In no instance did mock-vaccination with CM or any derivative produce protection against a TF challenge.

TF Obtained from Trophozoites

Sufficient numbers of radiation attenuated trophozoites injected intraperitoneally into mice had earlier been found to produce the toxic symptoms identical to TF as indicated in Table 4. Animal deaths were observed when the number of attenuated trophozoites was increased 100-fold. Although these deaths occurred within 1 week after intraperitoneal injection, similar to an acute infection with non-attenuated Toxoplasma The sonicate was centrifuged at 5,000×g 4° C. for 10 minutes. The supernatant was decanted and the pellet washed 2 times in PBS by centrifugation. The final pellet was resuspended in PBS to the original volume as stored. It was determined that TF could be recovered from sonicated preparations of glass fiber filtration purified liquid nitrogen stored trophozoites. Both the supernatant and the resuspended pellet from these sonicated organisms produced toxic symptoms indentical to TF. As shown in Table 4, this exposure protected mice against a challenge with TF.

TABLE 4

Summary of Actively Acquired Protection

| First Exposure | | Second Exposure | | |
|---|---|---|---|---|
| | Response | | Response | |
| Material | Weight Loss | Material | Day post 1st Exposure | Weight Loss | Loss of Reproduction |
| TF[a] | Yes | TF[a] | 21-27 | No[h] | — |
| TF | Yes | TF | 35 | — | No[i] |
| TF | Yes | CM | 21-27 | No | — |
| TF | Yes | CM | 35 | — | No |
| CM[b] | No | TF | 21-27 | Yes | — |
| CM | No | TF | 35 | — | Yes |
| CM | No | CM | 21-27 | No | — |
| CM | No | CM | 35 | — | No |
| TF | Yes | TF | 242 | No | — |
| CM | No | TF | 242 | Yes | — |
| TF (heat)[c] | No | TF | 28 | Yes | — |
| CM (heat)[c] | No | TF | 28 | Yes | — |
| TF (pH 2) | No | TF | 21 | Yes | — |
| TF (pH 5) | Yes | TF | 21 | No | — |
| TF (pH 9) | Yes | TF | 21 | No | — |
| TF (pH 12) | No | TF | 21 | Yes | — |
| ConATF[d] | Yes | ConATF | 28 | No[j] | — |
| ConATF | Yes | ConATF | 35 | — | No[k] |
| ConACM[e] | No | ConATF | 28 | Yes | — |
| ConACM | No | ConACM | 28 | No | — |
| ConACM | No | ConACM | 35 | — | No |
| Attenuated Trophozoites(AT)[f] | Yes | AT | 28 | No | — |
| AT | Yes | TF | 28 | No | — |
| TF | Yes | AT | 28 | No | — |
| Sonicated Trophozoites(ST)[g] | Yes | ST | 28 | No | — |
| ST | Yes | TF | 28 | No | — |
| TF | Yes | ST | 28 | No | — |

[a]approximately $10^4$ units
[b]diluted 1:1000/PBS
[c]56° C., 45 minutes
[d]approximately $10^3$ units
[e]diluted 1:1000/PBS
[f]$10^6$/mouse
[g]$>10^4$ units
[h]approximately 175 per test group (>95% protected)
[i]approximately 50 per test group (>95% of offspring surviving to weaning in vaccinated-challenged group compared to mock-challenged controls)
[j]approximately 50 per test group (>95% protected)
[k]approximately 20 per test group (>95% of offspring surviving to weaning in vaccinated-challenged group compared to mock vaccinated-mock challenged group)

trophozoites, the microscopic examination of peritoneal washings from these moribound mice revealed very few parasites.

These earlier observations suggested that TF may also be located within or on the trophozoites and it was the release of this material from the attenuated organisms in vivo which produce the toxic symptoms. These data suggest that TF may be obtained from animals infected with attenuated or non-attenuated Toxoplasma gondii.

Sonication of Purified Trophozoites

Trophozoites propagated in the BHK-21 cell line were purified by glass fiber filtration and stored in a liquid nitrogen freezer, thawed suspensions were sonicated (4° C.) at the maximum setting with a Fisher (Model 300) Dismembrator with microprobe for 10, 30 second periods with 30 seconds between sonications.

Passively Acquired Protection Against TF Adult Symptoms

Passive protection by neutralization of TF activity was examined by mixing equal volumes of (0.5 ml) anti-TF serum with 0.5 ml TF (1,000 units) 30 minutes prior to intraperitoneal injection of adult mice.

Anti-sera was produced in adult rabbits, Nys:(FG) by intramuscular injection of 20,000 units of TF in Freunds complete adjuvant. Two more injections, 3 weeks apart, of TF only were administered. Blood was taken from the ear vein 3 weeks after the last injection and the serum processed and stored frozen.

Mouse anti-ConATF serum was produced in mice by three bi-weekly intraperitoneal injections with approximately $10^4$ units. Three weeks after the last injection, the mice were bled by decapitation. The blood was combined and the serum stored frozen. Mouse anit-ConACM serum was prepared similarly.

Sera from rabbits immunized with TF was effective in neutralizing the toxic activity of TF (Table 5). Mice originally receiving rabbit anti-TF serum mixed with TF did not experience toxic symptoms, however, these mice were protected against re-challenge with active TF.

Mouse anti-ConATF sera was also determined to neutralize the toxic activity of ConATF, (Table 5) in adult mice.

TABLE 5

Summary of Passively Acquired Protection

| Serum | Material to Neutralize | Weight Loss Response |
|---|---|---|
| rabbit anti-TF | TF[a] | No[c] |
| rabbit anti-CM | TF | Yes |
| mouse anti-ConATF | ConATF[b] | No |
| mouse anti-ConACM | ConATF | Yes |

[a] approximately $10^4$ units
[b] approximately $10^3$ units
[c] ten mice per test group (all protected with anti-TF)

What is claimed is:

1. The method of preparing *Toxoplasma gondii* toxofactor (TF) the active immunogen of which is a glycoprotein in nature and has the following characteristics:

(a) is partially inactivated by heating at about 56° C. for about 30 minutes and completely inactivated by boiling for 1 hour;
   (b) is inactivated at extreme of pH values of 2 and 12 but is more stable at a pH of 5 to 8;
   (c) is partially inactivated when incubated with trypsin;

which is useful in protecting mammals from congential toxoplasmosis;

which comprises serially passing *Toxoplasma gondii* trophozoites in the peritoneal cavity of mice, aseptically isolating such infected peritoneal fluid, inoculating cell cultures with said fluid; propogating said trophozoites in a culture medium in vitro, harvesting the trophozoites and recovering a highly immunogenic toxplasmosis factor (TF) from the medium.

2. The method according to claim 1 in which the cell cultures are Baby Hamster Kidney cells.

3. The method of claim 1 wherein the toxofactor has the following additional characteristics:

(d) when injected intraperitoneally in non-immune mice produces transient signs and symptoms commonly observed with Toxoplasma injection in immunologically competent adults;
   (e) when injected intraperitoneally in non-immune pregnant mice on day 7 and 8, results in congential malformation and low birth weight in 60-90 percent of the litter; and
   (f) its biological effects are specifically neutralized by homologous or heterologous anti-serum.

* * * * *

UNITED STATES PATENT AND TRADEMARK OFFICE
CERTIFICATE OF CORRECTION

PATENT NO. : 4,564,592
DATED : January 14, 1986
INVENTOR(S) : Hassan A. Gaafar, et al.

It is certified that error appears in the above—identified patent and that said Letters Patent is hereby corrected as shown below:

Column 6, line 16: "firt two" should be --first two--

Columns 5-6 - Table 3 under the heading "total number": "229" should be --299--

Columns 7-8 - Table 4 after line 19 insert --ConACM No ConATF 35 --- Yes--

Columns 7-8 - Table 4 footnote e "diluted 1:1000/PBS" should be --diluted 1:100/PBS--

Column 9 - before claims insert --As indicated earlier, it is within the scope of the present invention to produce a toxoplasmosis vaccine, as an active form or an antigen-antibody mixture or as a toxoid. Such toxoids may be prepared in a conventional way by modifying with an appropriate agent such as formalin.--

Signed and Sealed this

Sixteenth Day of December, 1986

*Attest:*

DONALD J. QUIGG

*Attesting Officer*   *Commissioner of Patents and Trademarks*